US000001209H

United States Statutory Invention Registration [19]

[11] Reg. Number: H1209

Shiue et al.

[43] Published: Jul. 6, 1993

[54] NO-CARRIER-ADDED (18F)-N-METHYLSPIROPERIDOL

[75] Inventors: Chyng-Yann Shiue, East Setauket; Joanna S. Fowler, Bellport; Alfred P. Wolf, Setauket, all of N.Y.

[73] Assignee: The United States of America as represented by the United States Department of Energy, Washington, D.C.

[21] Appl. No.: 784,149

[22] Filed: Oct. 4, 1985

[51] Int. Cl.[5] ..... A61K 43/00
[52] U.S. Cl. ..... 424/1.1; 546/20
[58] Field of Search ..... 424/1.1, 9; 546/20

[56] References Cited

U.S. PATENT DOCUMENTS

| | | | |
|---|---|---|---|
| 2,348,231 | 6/1940 | Strain et al. | 260/476 |
| 3,155,670 | 11/1964 | Janssen | 260/294 |
| 3,981,769 | 9/1976 | Winchell et al. | 176/11 |
| 4,197,288 | 4/1980 | Snyder | 424/1 |
| 4,279,887 | 7/1981 | Baldwin et al. | 424/1.5 |
| 4,280,993 | 7/1981 | Braestrup et al. | 424/1 |
| 4,292,321 | 9/1981 | Pattison | 424/267 |
| 4,473,544 | 9/1984 | Machulla et al. | 424/1.1 |
| 4,656,280 | 4/1987 | Garlick | 546/20 |

FOREIGN PATENT DOCUMENTS

| | | | |
|---|---|---|---|
| 59-95288 | 6/1984 | Japan | 424/1.1 |
| 60-88384 | 9/1985 | Japan | 546/20 |
| 881893 | 11/1961 | United Kingdom | 546/20 |
| 1227965 | 4/1971 | United Kingdom | 546/20 |
| 2155473 | 9/1985 | United Kingdom | 546/20 |

OTHER PUBLICATIONS

Tewson et al, Brain Research, 192, 291–295 (1980).
Tewson et al, J. Labelled Compounds and Radiopharmaceuticals, XVIII, Nos. 1-2, 21-23, 102-103, (1980).
Wagner et al, Science, 221, 1264–1266 (1983).
Burns et al, J. Nuclear Medicine, 25(11), 1222–1227 (1984).

*Primary Examiner*—Robert L. Stoll
*Assistant Examiner*—Joseph D. Anthony
*Attorney, Agent, or Firm*—Margaret C. Bogosian; Paul A. Cottlieb; Judson R. Hightower

[57] ABSTRACT

There is disclosed a radioligand labeled with a positron emitting radionuclide suitable for dynamic study in living humans with positron emission transaxial tomography. [$^{18}$F]-N-methylspiroperidol, exhibiting extremely high affinity for the dopamine receptors, provides enhanced uptake and retention in the brain concomitant with reduced radiation burden. These characteristics all combine to provide [$^{18}$F]-N-methylspiroperidol as a radioligand superior to known radioligands for mapping dopamine receptors in normal and disease states in the living brain. Additionally, a new synthetic procedure for this material is disclosed.

2 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

2A, X=$NO_2$
2B, X=$(CH_3)_3\overset{+}{N}$ $I^-$
2C, X=$(CH_3)_3\overset{+}{N}$ $ClO_4^-$
a=Cs[$^{18}$F](NCA); b=▷ Li; c=HCl; d=KI, 3-methyl-1-phenyl-1,3,8-triazaspiro [4,5] decan-4-one.

NO-CARRIER-ADDED (18F)-N-METHYLSPIROPERIDOL

The U.S. Government has rights in this invention pursuant to Contract Number DE-AC02-76CH00016, between the U.S. Department of Energy and Associated Universities Inc.

BACKGROUND OF THE INVENTION

The present invention is directed to the synthesis of a radioligand, labeled with a positron emitting radionuclide which is suitable for dynamic studies in humans using positron emission transaxial tomography. The radio-labeled ligand, [$^{18}$F]-N-methylspiroperidol, exhibits extremely high affinity for dopamine receptors and provides enhanced uptake and retention in the brain concomitant with reduced radiation burden. These quantities all combine to make [$^{18}$F]-N-methylspiroperidol a radioligand superior to known radioligands used for mapping dopamine receptors in normal and diseased states in the living brain. Additionally, a synthetic procedure is disclosed to prepare this novel radioligand.

Recent advances in the study of neuropsychiatric diseases link manifestations of a disease to chemical changes in the brain. For example, the dopamine neurotransmitter has been linked with both Parkison's disease and schizophrenia as a source for altered synaptic transmission at the biochemical level.

The development of positron emission transaxial tomography (PETT) has now made it possible to study the dopamine receptors in a living brain. Radioligands labeled with positron emitting radionuclides permit quantitative studies based on annihilation radiation produced during positron emission. The technique consists of intravenous injection of a radioligand or radiopharmaceutical and subsequent imaging of the distribution of the radioactive label based on detection of the annihilation radiation produced during positron emission. For additional information on PETT, see Brownell, et al., *Science,* Vol. 215, pp 619–626 (1982).

Radioligands which have proved useful for such studies are those with a high in vivo affinity for the dopamine receptors, including [$^{11}$C]pimozide, [$^{18}$F]haloperidol, [$^{11}$C]spiroperidol, [$^{18}$F]spiroperidol, [$^{75}$Br]-, [$^{76}$Br]-, or [$^{77}$Br]bromospiroperidol, N-[$^{11}$C]methylspiroperidol, [$^{75}$Br]- or [$^{77}$Br] brombenperidol, [$^{75}$Br]- or [$^{77}$Br]bromperidol, $^{11}$C-labeled derivatives of 2-amino-6, 7-dihydroxy-1,2,3,4-tetrahydronaphthalene, and [$^{18}$F]benperidol.

Each radioligand exhibits significantly different properties. For example, while the brain uptake of haloperidol is higher than spiroperidol or benperidol, it is characterized by rapid egress and relatively high nonspecific binding. Both [$^{18}$F]spiroperidol and [$^{18}$F]benperidol cross the blood brain barrier to a lesser extent than [$^{18}$F]haloperidol, but are retained to a greater degree by the striatum, a region of high dopamine receptor density. This retention is stereospecific; it is prevented by prior administration of the dopamine antagonist (+)-butaclamol, but not by its pharmacologically inactive enantiomer (−)-butaclamol. Furthermore, with [$^{18}$F]spiroperidol, no clearance from the striatal areas is observed for up to 8 hrs. after injection. However, one potential problem of using [$^{18}$F]spiroperidol in human PATT studies is the relatively low uptake into the brain (0.5–1.0% of the injected dose in baboons) and consequently, the potentially high radiation burden required to obtain sufficiently high counting rates for PETT studies in humans.

The compound of the present invention, no-carrier-added (NCA) [$^{18}$F]-N-methylspiroperidol exhibits greater uptake into the brain's dopamine receptor rich areas than [$^{18}$F]-spiroperidol.

N-Methylspiroperidol, described in U.S. Pat. No. 3,155,670, was recently labeled in the N-methyl position with carbon-11 and shown to have a similar pharmacological profile to spiroperidol, although no quantitative information was presented on its brain uptake (see Wagner, et al., *Science.* Vol. 221, pp. 1264–1266 (1983). In that report, N-[$^{11}$C]methylspiroperidol was used to image dopamine receptors in baboons and in humans using PETT. While N-[$^{11}$C]methylspiroperidol, as well as [$^{11}$C]spiroperidol, offers some interesting possibilities in terms of certain experimental protocols involving repeat injections at short time intervals in the same experimental subject, both compounds have the disadvantage that they cannot be followed for more than about 2 hrs. on PETT, because of the short half-life of carbon-11 (20.4 min.). This is a time course which does not allow accurate determination of some kinetic parameters and does not afford maximum definition of specific receptor binding.

The present NCA [$^{18}$F]-N-methylspiroperidol, however, exhibits characteristics more suitable for use in PETT analyses than the above-noted compounds. Example 2 shows that the time course of distribution of NCA [$^{18}$F]-N-methylspiroperidol is more rapid than for [$^{18}$F]spiroperidol. Examples 3 and 5 disclose that the distribution and stability of NCA [$^{18}$F]-N-methylspiroperidol is superior to that of [$^{18}$F]spiroperidol.

As a further aspect of the present invention, NCA [$^{18}$F]-N-methylspiroperidol is produced by a new synthetic route more accomodating to the short half-life of the $^{18}$F-label. Other methods of producing the spiroperidol class of reagents are too long and involved to make use of an attached radionuclide.

SUMMARY OF THE INVENTION

Referring to FIG. 1, no-carrier-added (NCA) [$^{18}$F]-N-methylspiroperidol (4) is prepared from four different substrates: p-nitrobenzonitrile (1), cyclopropyl p-nitrophenyl ketone (2A), p-cyclopropanoyl-N,N,N-trimethylanilinium iodide (2B) and p-cyclopropanoyl-N,N,N-trimethylanilinium perchlorate (2C). The process for the production of NCA [$^{18}$F]-N-methylspiroperidol is a nucleophilic aromatic substitution reaction. The synthesis of 4 from 2A maximizes the product specific activity and experimental simplicity and provides 4 in 10–15% radiochemical yield (based on [$^{18}$F-]) with a mass of $<2$ nmol and a specific activity of $>10$ Ci/$\mu$mol (EOB).

Furthermore, the compound of this invention is shown to be effective as a new drug of choice in vivo examination of dopamine binding sites in a human brain. In particular, this drug is primarily useful in the noninvasive technique of positron emission transaxial tomography (PETT).

Utility Statement

The compound of this invention, NCA [$^{18}$F]-N-methylspiroperidol, is a positron emitting radiopharmaceutical or radioligand suitable for mapping dopamine receptors in normal and disease states in the living brain with positron emission transaxial tomography (PETT), a noninvasive imaging method for use in medical diagnosis and biological investigations.

Furthermore, a new synthetic route for production of the compound of this invention is useful as a method of producing similar radiopharmaceuticals with short half-lives.

DETAILED DESCRIPTION OF THE INVENTION

Figure 1:
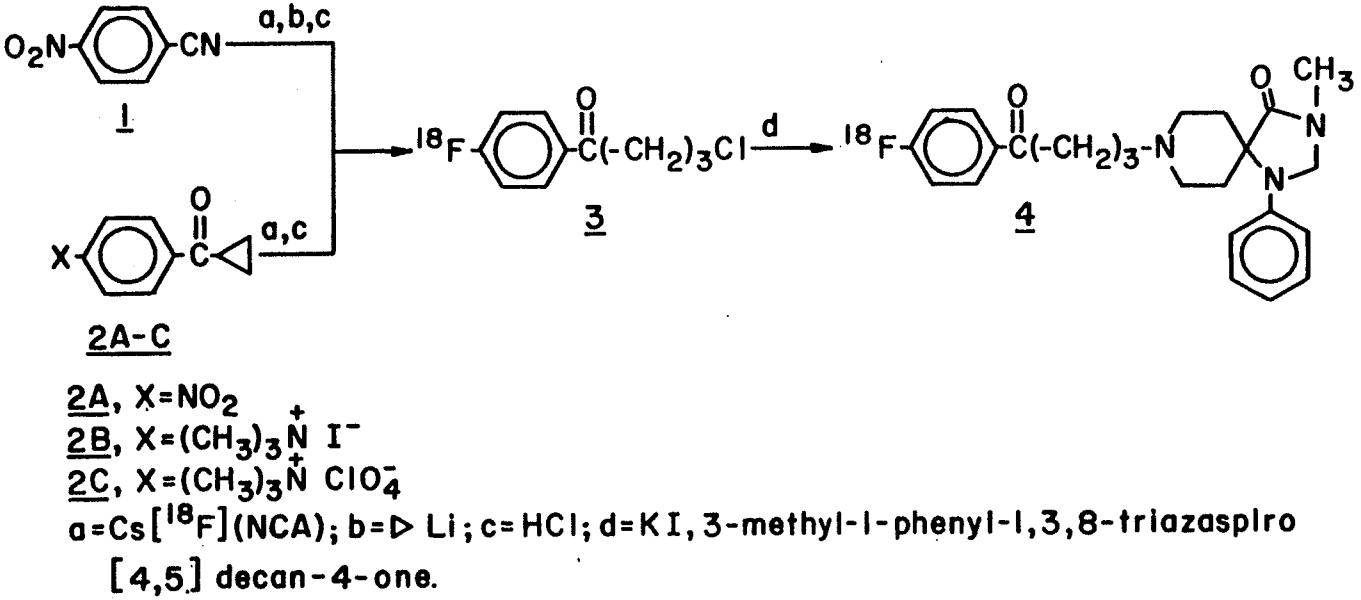
FIG. 1 Illustrates the methods of producing [$^{18}$F]-N-methylspiroperidol.

FIG. 1 Synthesis of NCA [$^{18}$F ]-N-methylspiroperidol (4) No-carrier-added [$^{18}$F]-N-methylspiroperidol is synthesized from four different substrates 1, 2A, 2B and 2C as shown in FIG. 1. The synthetic procedure using substrate 1 (Method A) differs considerably form the synthetic procedures using 2A, 2B, or 2C (Method B). Method A (Synthesis of 4 from 1): No-carrier-added aqueous [$^{18}$F]-fluoride (0.5 ml) prepared by the $^{18}$O(p,n)$^{18}$F reaction [Ruth, et al., *Radiochim Acta,* 26, 21–24 (1978) on a small volume of enriched water (95–99% $^{18}$O) target is added to a solution 1.8 mg of $Cs_2CO_3$ in 0.1 ml of water in an open pyrex vessel. The water is removed using a stream of nitrogen at 160° and coevaporated to dryness after adding $CN_3CH$ (2×0.5 ml). To the dried Cs[$^{18}$F] is added 2 mg of 1 in 0.2 ml of DMSO and a solution of 3 in pentane is obtained. The alkylation step is carried out using 3-methyl-1-phenyl-1,3,8-triazaspiro[4.5]decan-4-one (4 mg) and KI (8 mg). After alkylation, 0.5 ml of methanol and 4 ml of 2 N HCl are added to the crude reaction mixture and the solution is passed through a $C_{18}$ Sep-pak TM cartridge. The cartridge is then washed with water (5 ml) and pentane (5 ml). The crude product is eluted with 4 ml of $CH_2Cl_2$, which was filtered through a $K_2CO_3$ drying tube. The solvent is evaporated and the residue is dissolved in 0.5 ml of $CH_3OH$ and 0.5 ml of HO for preparative HPLC purification. The radiochemical yield of 4 synthesized by this method is 10–15% (based on total [$^{18}$F] fluoride delivered from the target) in a synthesis time of 120 min. from EOB. The total mass of the product is 2–5 nmol as determined by the UV absorbance of the radioactive peak as compared to a standard solution of N-methylspiroperidol. Thus, from 600 mCi of $^{18}$F, 60–90 mCi of 4 is obtained with the specific activity of 12–30 Ci/μmol at EOB, representing a $^{19}$F:$^{18}$F ratio in the range of 57–143 at EOB.

Method B: [$^{18}$R]-N-methylspiroperidol may also be synthesized from cyclopropyl p-nitrophenyl ketone (2A), p-cyclopropanoyl-N,N,N-trimethylanilinium (2B), or p-cyclopropanol-N,N,N-trimethylanilinium perchlorate (2C) using the nucleophilic aromatic substitution reaction shown in FIG. 1.

To dried Cs[$^{18}$F] (prepared as described above) in a platinum vessel is added a solution of 1–2 mg of 2A, 2B or 2C in 0.2 ml DMSO and the vessel is covered. This solution is heated at 160° for 2A (and 140° for 2B and 2C) for 10 min., cooled to room temperature and then 2 ml of a $CH_2OH$:HCl solution ($CH_3OH$;conc HCl, 1:1) is added. The mixture is heated at 110° for 5 minutes. Three ml of water is added and the mixture is transferred onto a $C_{18}$ Sep-pak TM cartridge prewashed with 3 ml of methanol followed by 4 ml of water. The Sep-pak TM cartridge is then washed with 4 ml of water and 0.5 ml of pentane. The product (γ-chloro-p-[$^{18}$F]fluorobutyrophenone) is eluted with 5 ml of pentane filtered through anhydrous $K_2CO_3$. The amine (3-methyl-1-phenyl-1,3,8-triazaspiro[4.5]decan-4-one, 3 mg) and KI (5–10 mg) are added to the dry pentane, a heating bath (140°) is applied and when the volume of the pentane is reduced to 0.2 ml, 0.5 ml of a 1:10 solution of DMF:THF is added and the mixture is heated for 10 minutes after THF evaporates. Methanol (0.5 ml) is added and the alkylation mixture is worked up as described in Method A and purified by preparation HPLC. Specific activity is determined as described above. In the synthesis of 4 from substrate 2A, 4-nitro-N-methylspiroperidol is produced and is well separated from 4 using the HPLC system described (retention times are 16 and 24 minutes respectively). Radiochemical yield of 4 using 2A, 2B and 2C are 10–15% at EOB. Synthesis times are 90 minutes. The use of substrate 2A produces a mass of <2 nmol and a specific activity of >10 Ci/μ mol (EOB) while the use of substrate 2B and 2C produces a mass of 20–70 nmol and a specific activity of 1 Ci/μmol (EOB). Radiochemical purity is >98% as determined by radioTLC in two solvent systems and by HPLC using both a normal phase silica gel column eluting with $CH_2Cl_2$:$CH_3OH$ (80:20) and a reversed phase $C_{18}$ column eluting either with $CH_3OH$:0.01M $(NH_4)_2HPO_4$ (70:30) or with $CH_3OH$:0.01M $NH_4HCO_2$ (65:35). No other radioactive peaks were observed on TLC or HPLC and all of the radioactivity was observed to co-elute with authentic compound 4 which were co-injected (or co-spotted) with samples of the $^{18}$F-labeled product.

Starting Materials

In the two synthesis processes described above, all of the starting elements are either known and commercially available, or produced by known processes.

Cesium carbonate, dimethylsulfoxide (DMSO), p-nitrobenzonitrile, 3-methyl-1-phenyl-1,3,8-triazaspiro[4.5] decan-4-one hydrochloride, and cyclopropyl p-fluorophenyl ketone are all available commercially.

Cyclopropyl lithium and cyclopropyl p-nitrophenyl ketone (2) are synthesized by known methods. See, for example, Seyferth et al, *J. Organomet. Chem.,* Vol. 1, pp 15–21 (1963) and Skiue et al, *J., Label. Cmpds. Radiopharm.,* Vol. 21, pp. 533–547 (1984).

Thin-layer chromatographic analyses (TLC) are performed on plastic-backed TLC plates (Merck) with either $CH_3CN$:$CH_3OH$ (4:1) or $CH_2CL_2$:$CH_3OH$ (9:1) as solvent. HPLC analyses are carried out with a Perkin-Elmer Series 3B liquid chromatograph equipped with a radioactivity monitor (Berthold Model LB503). An analytical reversed phase $C_{18}$ column (4.5×250 mm) is preferred with either $CH_3OH$:0.01M $(NH_4)_2HPO_4$ (70:30) or $CH_3OH$:0.01M $NH_4HCO_2$ (65:35) as the solvent (flow rate of 2 ml/min). For the preparative separations, a semi-preparative $C_{18}$ column (10×250 mm) is used with $CH_3OH$:0.01M $NH_4HCO_2$ (65:35) as the solvent (flow rate of 6 ml/min). The $C_{18}$ Sep-pak TM cartridges are commercially available from Waters Associates.

The synthesis of substrates 2B and 2C are as follows:

Synthesis of p-Cyclopropanoyl N,N,N-Trimethylanilinium Iodide (2B)

p-N,N-Dimethylaminophenyl cyclopropyl ketone (186.50 mg, 0.99 mmol) is added to 2 ml of dimethylformamide (DMF). Methyl iodide (0.24 g, 7.4 mmol) is added to the solution, the flask stoppered and the solution stirred for 18 hrs. Ethyl acetate is added to the flask to precipitate the product and the solution is filtered. The precipitate is washed with ethyl acetate, ether and chloroform. The precipitate is then dissolved in a minimal amount of methanol and filtered. Ether is added to the filtrate to precipitate the product. The product is filtered and washed with ether and dried. This yielded 2B as a white crystalline solid (56.25 mg, 17.2% yield); m.p. >280° C.; IR (KBr):1660 $cm^{-1}$ (C=O): NMR ($CD_3CN$) δ:1.15 (d, 4H); 2.60 (m, 1H ); 3.61 (s, 9H); 7.93 (d, 2H); 8.24 (d, 2H); mass spectrum m/e=189 (M-$CH_3I$). Calculated for $C_{13}H_{18}ION$:C, 47.14; H, 5.49; I, 38.31, N, 4.23. Found: C, 45.60; H, 5.49; I 38.91; N, 4.50. HPLC analysis of the product show that no cyclopropyl p-fluorophenyl ketone is present in the final product.

The synthesis of the starting material, p-N-N-Dimethylaminophenyl cyclopropyl ketone, follows a modification of Freed et al, U.S. Pat. No. 3,268,553.

Cyclopropyl p-fluorophenyl ketone (1.12 g, 6.9 mmol) is added to 3 ml of dimethylsulfoxide (DMSO). The flask is sealed with a septum and the solution stirred and cooled to 0° C. in an ice bath. Anhydrous dimethylamine (3.4 g, 75.5 mmol) is added by syringe and the solution is gradually warmed to room temperature and allowed to stir at room temperature for 72 hrs. The precipitate is filtered and washed with DMSO and ether. Recrystallization from acetone-pentane (1:1) yielded p-N,N-dimethylaminophenyl cyclopropyl ketone as a white crystalline solid (1.22 g, 92.8%); m.p. 139°-141° C.; IR (KBr):158 $cm^{-1}$ (C=O); NMR ($CDCl_3$) δ:0.99 (m,2H); 1.16 (m,2H ) 2.60 (m,1H); 3.05 (s,6H); 6.67 (d,2H); 7.96 (d,2H).

Synthesis of p-Cyclopropanoyl-N,N,N-Trimethylanilinium Perchlorate (2C)

Compound 2C is prepared by the method of Kevill et al, *J. Am. Chem. Soc.*, Vol. 103, pp 4515-4521 (1983). Anhydrous silver perchlorate (116.9 mg, 0.56 mmol) is placed in a three neck round bottom flask with a condenser and an addition funnel and the apparatus is purged with dry nitrogen. Benzene (2 ml) is added to the flask and the solution is stirred. Methyl iodide (79.57 mg, 0.56 mmol in 1 ml benzene) is added dropwise over a period of 15 minutes and the solution is stirred at room temperature for 4 hours. The mixture is filtered and passed through a short column of 4 A molecular sieves. The filter is washed with 2 ml of benzene and the filtrate and washings are collected in a flask which contained p-N,N-dimethylaminophenyl cyclopropyl ketone (113.48 mg, 0.6 mmol). The flask is purged with nitrogen, sealed and stirred at room temperature for 2 weeks. The mixture is then filtered and the residue washed with benzene and chloroform. The residue is dissolved in acetonitrile and the solution filtered. Ether is added to the filtrate to precipitate the product. The product is filtered, washed with ether, and dried in a vacuum oven. This method produces 11.94 mg (7.1%) of compound 2C as a white crystal; m.p. 174°-175° C.; IR (KBr); 1655 $cm^{-1}$ (C=O); 1095 $cm^{-1}$ (Cl-O); NMR ($CD_3CN$) δ1.14 (d,4H); 2.84 (m,1H); 3.60 (s,9H); 7.92 (d,2H); 8.22 (d,2H); mass spectrum m/e=189 (M-$CH_3CO_4$). Calculated for $C_{13}H_{18}C10_5N$:C, 51.40; H, 5.98; N,4.61. Found: C, 50.09; H, 6.38; N, 4.67. Sodium fusion of a small sample of the product and analysis for fluoride indicates no fluorine contamination in the product.

EXAMPLE 1

PETT Baboon Studies

A young adult (12 kg) female baboon (Papio anubis) was anesthesized initially with ketamine and subsequently maintained under halothane/nitrous oxide anesthesia for two PETT studies. In the first study, the animal was pretreated with 0.5 mg/kg of (−)-butaclamol, i.v., 39 mins before injection of 11 mCi of [$^{18}$F]-N-methylspiroperidol. In the second study (three weeks later), the same baboon was pretreated with 0.5 mg/kg of (+)-butaclamol, i.v., 26 mins before injection of 10 mCi of [$^{18}$ F]-N-methylspiroperidol. Pett scans were made continually for 4 hrs from the time of radioisotope injection.

Figure 2:
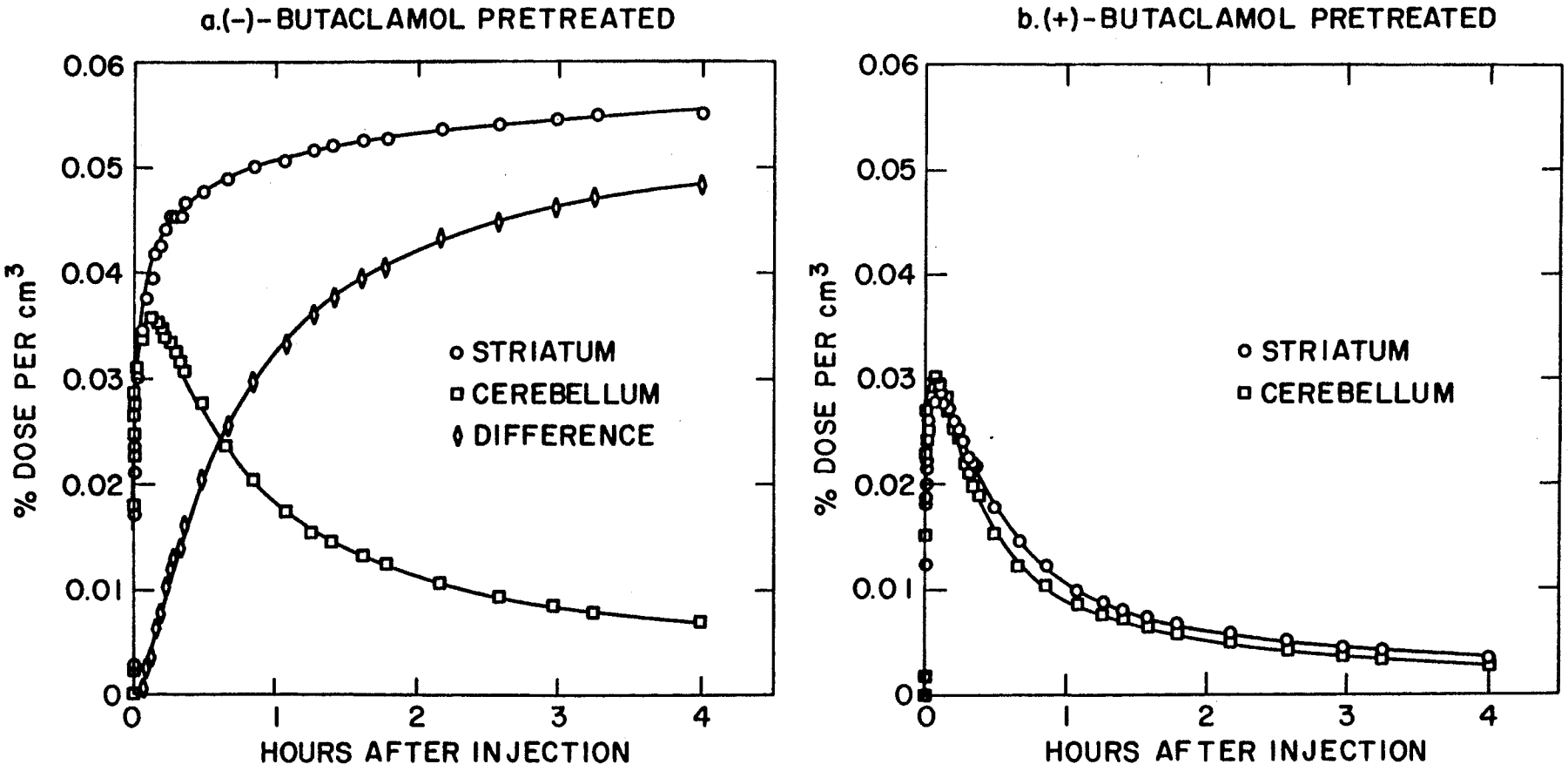
FIGS. 2(*a* and *b*) Baboon striatum and cerebellum radioactivity concentrations determined from PETT scans after injection of [$^{18}$F]-N-methylspiroperidol. (a) Control study following 0.5 mg/kg of (−)-butaclamol pretreatment, showing the normal distribution of radioligand. (b) Receptor-blocked study, showing the effect of stereospecific blocking of dopamine receptors in the striatum by pretreatment with 0.5 mg/kg of (+)-butaclamol.

FIG. 2*a* shows the distribution of [$^{18}$F]-N-methylspiroperidol to striatum and cerebellum of the baboon in the control study, following pretreatment with the inactive (−)-enantiomer of butaclamol. The absolute striatal uptake for this compound exceeded that for [$^{18}$F]spiroperidol by more than two-fold. Influx into both brain regions was equal for the first few minutes, but radioactivity then declined rapidly in the cerebellum, while increasing for up to 4 hrs in the striatum. If one takes the difference between radioactivities in striatum and cerebellum (labeled "DIFFERENCE" in FIG. 2*a*) as a measure of the specifically bound component of radioactivity in the striatum, then the specifically bound component of radioactivity was still increasing at 4 hrs after injection, as was found for [$^{18}$F]spiroperidol.

Pretreatment of this animal with the same dose of the pharmacologically active (+)-enantiomer of butaclamol produced the results shown in FIG. 2*b*. The striatum and cerebellum radioactivity curves are superimposable, indicating that the radioligand no longer had access to specific binding sites. This demonstrates the stereospecificity of the striatal retention of radioactivity in (a), and supports the contention that the cerebellum curve in (a) is a reasonable approximation of the nonspecifically bound and free components of radioactivity included in the striatum curve.

EXAMPLE 2

Baboon Plasma Analyses

Blood was sampled from the femoral artery at initial intervals of 5 secs. Aliquots of plasma were counted to determine the total plasma radioactivity of clearance curves. Representative samples (see Table 1) were also analyzed for unchanged [$^{18}$F]-N-methylspiroperidol by a rapid separation procedure using a mixture of $CH_2Cl_2$:$CH_3OH$, 9:1 by volume, to develop the TLC used to separate components in the $CH_3CN$ eluate from the C-18 Sep-pak TM cartridge. This system was chosen to allow adequate separation of [$^{18}$F]-N-methylspiroperidol ($R_f$=0.62) from its possible radioactive metabolite, [$^{18}$F] spiroperidol ($R_f$=0.46).

Figure 3:
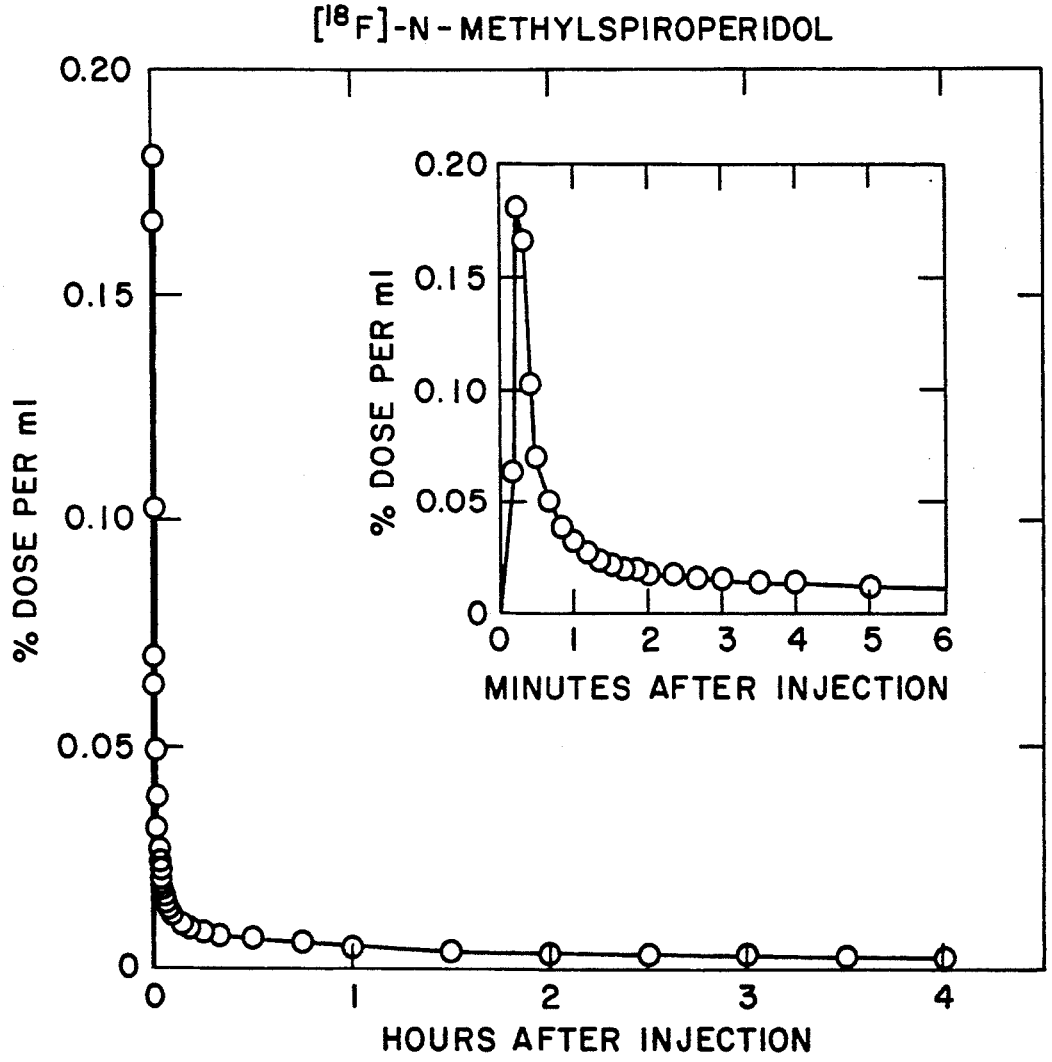
FIG. 3 Blood plasma total radioactivity clearance curve for [$^{18}$F]-N-methylspiroperidol in the baboon. Each point is the average from the two studies depicted in FIG. 2. The range of values for the two studies was less than 0.003% dose per ml for each time after 2 min.

The baboon blood total plasma radioactivity clearance curve is depicted in FIG. 3. As with other $^{18}$F-labeled butyrophenones, the blood clearance was very rapid, dropping to lower than the brain concentration in the first 90 secs after injection. The appearance of metabolites in the blood was also rapid (Table 1). At 10 mins after injection only 43% of plasma radioactivity was due to unaltered [$^{18}$F]-N-methylspiroperidol. The corresponding value for [$^{18}$F]spiroperidol was 72% unchanged, indicating that the appearance of peripheral radioactive metabolites is more rapid for the N-methyl derivative.

EXAMPLE 3

To investigate the metabolic stability of [$^{18}$F]-N-methylspiroperidol in the central nervous system, its stability in rat brain studied (Table 2). As with [$^{18}$F]spiroperidol, very little metabolism of this compound was found in the rat brain, with the absolute amount in the striatum remaining constant from 1 to 4 hrs after injection. However, rat striatal uptake of the N-methyl radioligand was five-fold higher than with [$^{18}$F]spiroperidol.

Four male BNL R strain rats (350–380 g) (Brookhaven National Laboratory, Upton, N.Y.) were injected with 1.4 to 1.8 mCi of [$^{18}$F]-N-methylspiroperidol, i.v. At 1 or 4 hrs after injection (2 animals each), the animal was killed and the combined striata and cerebellum were separately counted and homogenized in a mixture of 1 ml of MeOH and 2 ml of 0.4M $HClO_4$. The samples were centrifuged, and the entire supernates were analyzed for unchanged [$^{18}$F]-N-methylspiroperidol.

EXAMPLE 4

Comparison of the Synthesis of $^{18}$F-Labeled N-methylspiroperidol (4) from 1, 2A, 2B and 2C Four criteria, radiochemical yield, experimental simplicity, synthesis time and specific activity were used in comparing the synthesis of 4 from substrates 1, 2A, 2B and 2C. With respect to radiochemical yield, comparable yields (10–15%) were obtained from each substrate. On the other hand, the experimental procedure using 2A–C was far simpler than that for 1 and the relative synthesis times (90 mins vs 120 mins) were different.

The effects of temperature, reaction times and acid concentration on the conversion of cyclopropyl p-[$^{18}$F]fluorophenyl ketone to γ-chloro-p-[$^{18}$F] fluorobutyrophenone 3 were also investigated (Table 3). The optimal conditions for this reaction were 110° C. for 3–5 mins which gave compound 3 in 85% radiochemical yield.

Based on the observations the use of 2A optimizes specific activity and ease of synthesis. It is effectively a one pot synthesis for the Cs[$^{18}$F] displacement and hydrolysis. Two $C_{18}$ Sep-pak TM cartridges are used. HPLC purification is straightforward with 4-nitro-N-methylspiroperidol, (5), a by-product of the reaction, being well separated from N-methylspiroperidol using a $C_{18}$ semipreparative column.

EXAMPLE 5

Tissue Distribution

Table 4 shows the distribution of radioactivity in various mouse tissues at 5, 60, and 120 min after injecting $^{18}$F-labelled N-methylspiroperidol (4). As noted in Example 3 for the rat, the mouse brain uptake of radioactivity was higher for radiolabeled N-methylspiroperidol (1.1% of the administered dose). A comparison of the mouse tissue distribution of radioactivity following injection of $^{18}$F-labeled N-methylspiroperidol (4) (Table 4) with the radioactivity tissue distribution reported for N-[$^{11}$C] methylspiroperidol shows very little difference. It is believed that N-[$^{11}$C] methylspiroperidol, with the radiolabel on the amine portion of the molecule, shows a radioactivity distribution in vivo which is markedly different form that of $^{18}$F-labeled N-methylspiroperidol, which is radiolabeled on the B-(4-fluorobenzoyl) propionic acid portion.

TABLE 1

Analyses of $^{18}$F Radioactivity in Baboon Plasma Samples

| Min After Injection | $H_2O$ Eluate | NaOH Eluate | $CH_3CN$ Eluate | % of $^{18}$F in $CH_3CN$ as [$^{18}$F]-N-Methylspiroperidol | % [$^{18}$F]-N-Methylspiroperidol in Plasma |
|---|---|---|---|---|---|
| 0.67 | 0.5 | 0.2 | 92 | 88 | 81 |
| 4.0 | 1.8 | 6.3 | 85 | 78 | 66 |
| 10 | 3.2 | 14 | 73 | 60 | 43 |
| 30 | 7.4 | 25 | 56 | 32 | 18 |
| 60 | 9.9 | 30 | 51 | 36 | 18 |
| 120 | 15 | 30 | 41 | 26 | 11 |
| 180 | 11 | 39 | 37 | 29 | 11 |
| 240 | 13 | 35 | 36 | 26 | 9.4 |

TABLE 2

Metabolic Stability of [$^{18}$F]-N-Methylspiroperidol in Rat Brain (n = 2)

| | Hours After Injection | Ave. & Inj. Dose per Region (Ind. Values) | Ave. % of Total Radioactivity Extracted (Ind. Values) | Ave. % of Extracted Radioactivity as Unchanged [$^{18}$F]-N-Methylspiroperidol (Ind. Values) |
|---|---|---|---|---|
| Striatum | 1 | 0.0662 (0.0712, 0.0612) | 89 (88, 90) | 96 (95, 96) |
| | 4 | 0.0688 (0.0723, 0.0653) | 88 (88, 88) | 98 (98, 97) |
| Cerebellum | 1 | 0.0145 (0.0149, 0.0141) | 74 (74, 74) | 90 (90, 90) |
| | 4 | 0.0024 (0.0025, 0.0024) | 76 (77, 74) | 85 (85, 85) |

TABLE 3

The Effects of Temperature, Reaction Time and Acid Concentration on the Conversion of Cyclopropyl p-Fluorophenyl Ketone to δ-chloro-p-fluorobutyrophenone

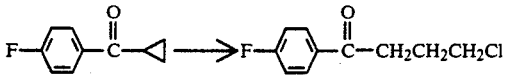

| Temperature (°C.) | Time (Min) | Conc. HCl—MeOH | Yield (%) |
|---|---|---|---|
| 80 | 5 | 1:1 | 65.2 |
| 80 | 10 | " | 75.2 |
| 80 | 20 | " | 84.0 |
| 100 | 5 | " | 83.2 |
| 100 | 10 | " | 82.2 |
| 110 | 3 | " | 84.9 |

TABLE 3-continued

The Effects of Temperature, Reaction Time and Acid Concentration on the Conversion of Cyclopropyl p-Fluorophenyl Ketone to δ-chloro-p-fluorobutyrophenone

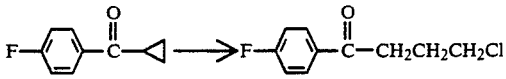

| Temperature (°C.) | Time (Min) | Conc. HCl—MeOH | Yield (%) |
|---|---|---|---|
| " | 5 | " | 83.1 |
| " | 10 | " | 77.9 |
| " | 20 | " | 65.4 |
| " | 3 | 1:3 | 21.2 |

TABLE 4

Tissue Distribution of [$^{18}$F]-N-Methylspiroperidol in Mice

| | Time After Injection (Min) | | | | | |
|---|---|---|---|---|---|---|
| | 5[a] | | 60[a] | | 120[b] | |
| Tissue | % Dose/g | % Dose/Organ | % Dose/g | % Dose/Organ | % Dose/g | % Dose/Organ |
| Brain | 2.3 (2.2–2.4) | 1.1 (1.0–1.1) | 1.5 (1.3–1.8) | 0.68 (0.60–0.74) | 1.3 (1.1–1.6) | 0.57 (0.43–0.68) |
| Blood | 1.2 (1.0–1.5) | | 0.45 (0.40–0.50) | | 0.19 (0.15–0.27) | |
| Heart | 3.3 (3.2–3.4) | 0.37 (0.35–0.42) | 0.61 (0.59–0.65) | 0.072 (0.064–0.076) | 0.24 (0.18–0.35) | 0.026 (0.020–0.030) |
| Lungs | 13 (11–14) | 2.0 (2.0–2.1) | 1.9 (1.6–2.3) | 0.27 (0.24–0.29) | 0.95 (0.70–1.50) | 0.12 (0.09–0.16) |
| Liver | 5.4 (5.2–5.7) | 8.2 (8.2–8.3) | 2.9 (2.4–3.4) | 4.0 (3.8–4.1) | 1.4 (1.2–1.9) | 1.6 (1.5–1.8) |
| Spleen | 5.8 (4.7–6.5) | 0.95 (0.82–1.05) | 1.6 (1.1–1.9) | 0.26 (0.25–0.28) | 0.57 (0.40–0.73) | 0.062 (0.043–0.073) |
| Kidneys | 12 (11–13) | 4.5 (4.2–4.8) | 3.4 (3.0–4.0) | 1.2 (1.1–1.3) | 1.5 (1.2–1.8) | 0.46 (0.40–0.57) |
| Small Intestine | 4.3 (4.0–4.8) | 5.3 (3.2–6.8) | 2.5 (1.7–3.4) | 2.9 (1.6–3.6) | 1.3 (0.8–1.7) | 1.3 (0.7–1.9) |
| Ovaries | | 0.12c (0.11–0.12) | | 0.040 (0.028–0.057) | | 0.014 (0.009–0.022) |

[a]Mean (range) of three mice.
[b]Mean (range) of four mice.
[c]Mean (individual values) of two mice.

We claim:

1. No-Carrier-Added [$^{18}$F]-N-methylspiroperidol.

2. The use of NCA-[$^{18}$F]-N-methylspiroperidol as the radiolabeled material in a positron emission transaxial tomographic procedure to map dopamine receptors in normal and disease states in the living brain whereby an effective amount of said NCA-[$^{18}$F]-N-methylspiroperidol is intravenously injected into the subject and the dopamine receptors are mapped using a positron emission tomography scanner.

* * * * *